United States Patent [19]
Padden et al.

[11] Patent Number: 5,464,383
[45] Date of Patent: Nov. 7, 1995

[54] DEVICE FOR SUPPORTING AND IMMOBILIZING A PATIENT'S ARM AND SHOULDER AND METHOD THEREFOR

[76] Inventors: John Padden, 214 E. Ruth Ave., #303, Phoenix, Ariz. 85020; Michael A. Steingard, 8602 N. Starling La., Phoenix, Ariz. 85028

[21] Appl. No.: 284,843

[22] Filed: Aug. 2, 1994

[51] Int. Cl.[6] .................................................. A61F 5/00
[52] U.S. Cl. ........................... 602/20; 602/4; 128/878
[58] Field of Search ..................... 128/878, 889, 128/892, 882, 881, 869, 846, 845, DIG. 20, DIG. 19; 602/20, 19, 13, 5, 4, 6, 62, 61, 60; 2/16, 59, 126

[56] References Cited

U.S. PATENT DOCUMENTS

| | | | |
|---|---|---|---|
| 3,745,998 | 7/1973 | Rose | 602/6 |
| 4,232,664 | 11/1980 | Blatt | 602/4 |
| 4,375,809 | 3/1983 | Meals | 128/878 |
| 4,598,701 | 7/1986 | Schaefer | 602/19 |
| 4,836,195 | 6/1989 | Berrehail | 602/19 |
| 4,896,660 | 1/1990 | Scott | 602/20 |
| 4,971,041 | 11/1990 | Millikan et al. | 128/878 |
| 5,048,542 | 9/1991 | Murray | 128/889 |
| 5,236,411 | 8/1993 | Backman | 128/845 |
| 5,291,903 | 3/1994 | Reeves | 128/845 |
| 5,334,132 | 8/1994 | Burkehead | 602/4 |

FOREIGN PATENT DOCUMENTS

| | | | |
|---|---|---|---|
| 2589722 | 5/1987 | France | 602/13 |
| 2619307 | 2/1989 | France | 602/20 |
| 3517343 | 11/1986 | Germany | 602/20 |
| 3827981 | 2/1990 | Germany | 602/20 |

Primary Examiner—Robert A. Hafer
Assistant Examiner—Michael O'Neill
Attorney, Agent, or Firm—Harry M. Weiss; Jeffrey D. Moy; A. J. Moss

[57] ABSTRACT

An orthopedic pillow device for supporting and immobilizing patient's arm relative to a patient's shoulder is disclosed comprising a portable, L-shaped, reversible, pillow and a plurality of straps for attaching and securing the pillow to both the patient's upper torso and arm. The pillow is selectively attached to one of the patient's right arm and left arm and the patient's upper torso, for providing support and cushioning for both a lower and upper portion of the arm selected for support and for providing abduction of the arm selected for support with respect to the upper torso for reducing shoulder joint stress. The securing means is comprised of a removable shoulder strap, waist strap, forearm strap and upper arm strap.

20 Claims, 2 Drawing Sheets

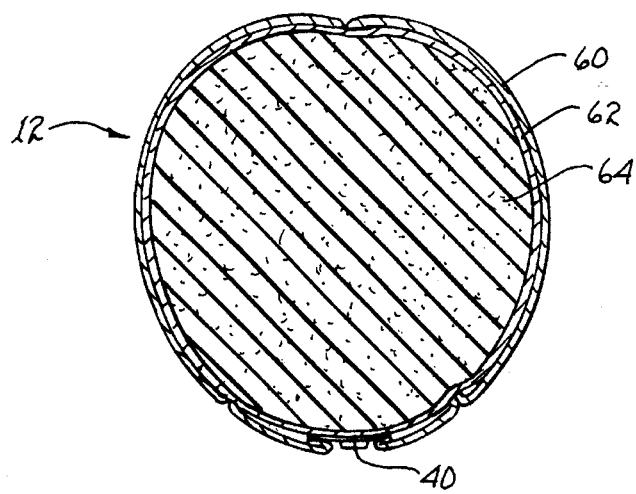
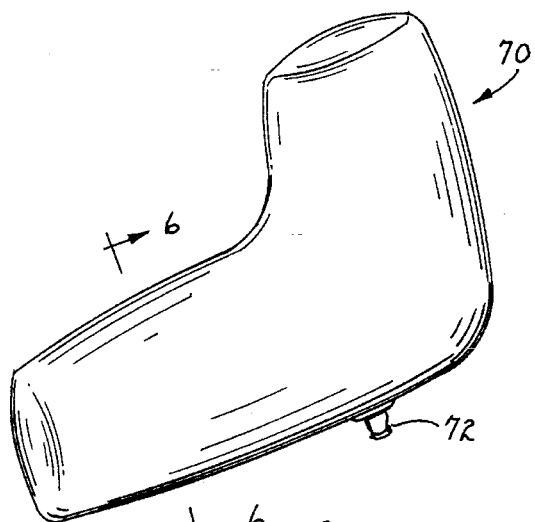
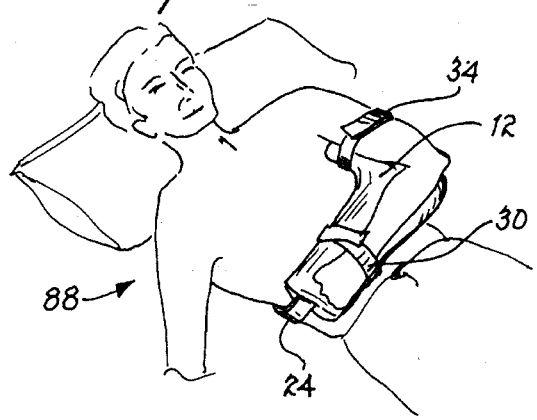
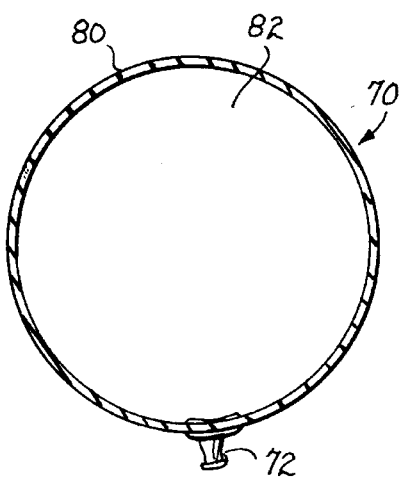
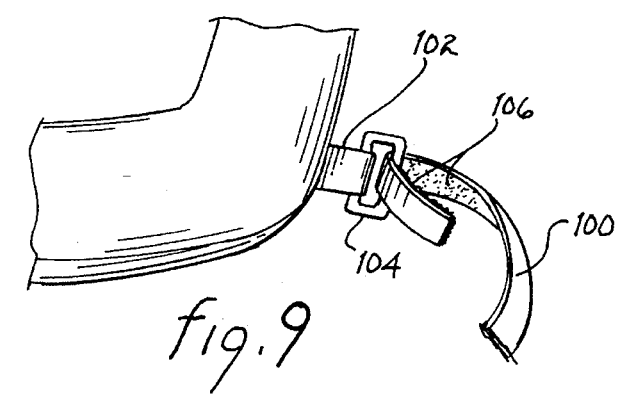

DEVICE FOR SUPPORTING AND IMMOBILIZING A PATIENT'S ARM AND SHOULDER AND METHOD THEREFOR

BACKGROUND OF THE INVENTION

1. Field of the Invention

This invention relates generally to orthopedic devices and methods therefor, and more specifically relates to improved orthopedic pillow support devices used to hold, support, cushion and immobilize a patient's injured arm or a patient's arm with respect to a patient's injured shoulder and methods therefor.

2. Description of the Related Art

In the past, various types of orthopedic devices were created to support an arm and/or shoulder during post-surgical or non-surgical recovery from injury. These devices are often used prior to surgery as well. For example, to aid in the healing of and to provide relief to a shoulder suffering from any number of ailments such as a rotator cuff injury, sprains, dislocations, humeral fractures and other injuries, it is critical to stabilize and immobilize the respective forearm and upper arm at a desired position with respect to the injured shoulder to prevent shoulder joint movement. It is further necessary to position the arm away from the upper torso at an abduction angle that is most conducive to reducing shoulder joint stress. It is also important to provide such support during both waking and sleeping hours while providing the utmost comfort and convenience to the patient.

The prior art includes a number of orthopedic devices for supporting an arm and shoulder. For example, one familiar device is the arm sling. It is simply comprised of material in which an arm, typically bent at the elbow at approximately a ninety degree angle, is placed and a shoulder strap for holding the material and arm in place. This type of device provides minimal arm and shoulder support but provides no immobilization of the arm and shoulder joints. It also generally does not provide cushioning for comfort.

U.S. Pat. No. 4,373,517 describes a device that supports an arm and immobilizes a shoulder. It is essentially a metal brace comprised of multiple rigid assemblies mounted to a patient's torso to support a rigid horizontal member, which, in turn, supports an arm in a horizontal-only position. This device suffers from numerous drawbacks. It is a complex device comprised of many rigid, metal parts and is consequently bulky, heavy, uncomfortable and not conducive for wearing over long periods of time. Furthermore, it limits the position of the arm to substantially the horizontal plane making it inflexible and unable to be worn in the recumbent (lying down) position. Therefore, a patient who needed the benefits of this device around the clock had to either remove the device to sleep in the recumbent position or sleep in an uncomfortable upright position.

Another orthopedic device developed was a shoulder immobilizer which provided a sling-type apparatus to hold an arm and a separate pillow device wrapped around a patient's waist upon which the arm rests. Weaknesses of this two piece device are that it is only utilized for post-surgery situations and is not designed for recumbent use.

Moreover, none of the prior devices provided much versatility in terms of their application to a variety of injuries and conditions, flexibility of positioning the arm with respect to the patient's body, ease of use, and comfort, all in one device.

Accordingly, there existed a definite need to provide a new orthopedic support device that would be useful for a shoulder injury, arm injury or both, portable and lightweight, extremely comfortable to wear, easy to attach to the body, reversible for attachment to either the left arm and shoulder or right arm and shoulder, adjustable to the size of the patient and to the desired position, and easier and less costly to manufacture. This device would be versatile enough for use in a wide variety of orthopedic applications ranging from non-surgical type arm or shoulder sprains, dislocations and fractures to post-surgical recovery periods such as that after a rotator cuff surgery or other shoulder surgeries. Furthermore, since patients who must wear the devices of the prior art to sleep must remain in the upright, sitting position, it was especially important to provide a device that could be worn in the recumbent, as well as upright, positions.

SUMMARY OF THE INVENTION

In accordance with one embodiment of this invention, it is an object of this invention to provide an improved, reversible, orthopedic arm and shoulder support device that immobilizes both the shoulder and arm joints and provides abduction of the arm for reducing shoulder joint stress.

It is another object of this invention to provide a new orthopedic pillow support device that is light, low cost, easy to attach to the body and comfortable to wear.

It is a further object of this invention to provide an orthopedic arm and shoulder pillow device for use while the patient is in the recumbent, as well as upright, positions.

It is yet another object of this invention to provide a method for a new and improved, reversible, orthopedic arm and shoulder support device that immobilizes both the shoulder and arm joints.

BRIEF DESCRIPTION OF THE PREFERRED EMBODIMENTS

In accordance with one embodiment of this invention, an orthopedic pillow device for supporting and immobilizing a patient's arm relative to a patient's shoulder is disclosed comprising, in combination, a portable, reversible, pillow support means for selective attachment to one of the patient's right arm and left arm and the patient's upper torso, wherein the support means comprises an L-shape pillow means for providing support and cushioning for both a lower and upper portion of the arm selected for support, and for providing abduction of the lower and upper portions of the arm selected for support with respect to the upper torso for reducing joint stress in the shoulder, and a securing means coupled to the support means for securing the support means to both the patient's arm and upper torso.

The support means comprises an inner material having a long member coupled at one end thereof to one end of a short member forming an L-shape, and an outer casing conforming to the L-shape of the inner material for containing the inner material. The inner material comprises a fiberfill material stuffed in a casing. The outer casing comprises a zipper means for providing access to the inner material for removing the inner material from the outer casing.

The securing means comprises a first strap means for securing the support means to the patient's upper torso and a second strap means for securing the support means to the patient's arm. The first strap means comprises a waist strap coupled to the long member of the support means for securing to a portion of the patient's waist and a shoulder strap coupled at one end thereof to the unconnected end of the long member and coupled at the other end thereof to the unconnected end of the short member for securing the support means to the patient's shoulder. The shoulder strap is removable. The second strap means comprises an upper arm strap coupled to the short member for securing the upper arm to the support means and a forearm strap coupled to the long member for securing a portion of the patient's forearm to the support means. The forearm strap is removably connected to the long member of the support means for placement at any one location along the long member.

In accordance with another embodiment of this invention, an orthopedic pillow support device is disclosed wherein the inner material is comprised of a pre-formed foam material.

In accordance with yet another embodiment of this invention, an orthopedic pillow device is disclosed wherein the inner material is comprised of an inflatable air bladder.

In accordance with still another embodiment of this invention, a method of providing an orthopedic arm and shoulder support device is disclosed, comprising the steps of providing a portable, reversible, pillow support means for selective attachment to one of the patient's right arm and left arm and the patient's upper torso, the support means comprising an L-shape pillow means for providing support and cushioning for both a lower and upper portion of the arm selected for support, and a securing means coupled to the support means for securing the support means to both the patient's arm and upper torso.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 4 is a cross sectional view of the long member of the support device of FIG. 1 taken along the line 4—4 showing a fiberfill inner material or a pre-formed foam material.

FIG. 5 is a perspective view of the pillow support member of FIG. 1 in another embodiment providing an inflatable air bladder for the inner material.

FIG. 6 is a cross sectional view of the long member of the support device of FIG. 5 taken along the line 6—6.

FIG. 7 is a perspective view of the support device of FIG. 1 as worn by a person in the recumbent position.

FIG. 9 is a perspective view of another embodiment of the waist strap of the support device of FIG. 1.

DESCRIPTION OF THE PREFERRED EMBODIMENTS

Figure 1:
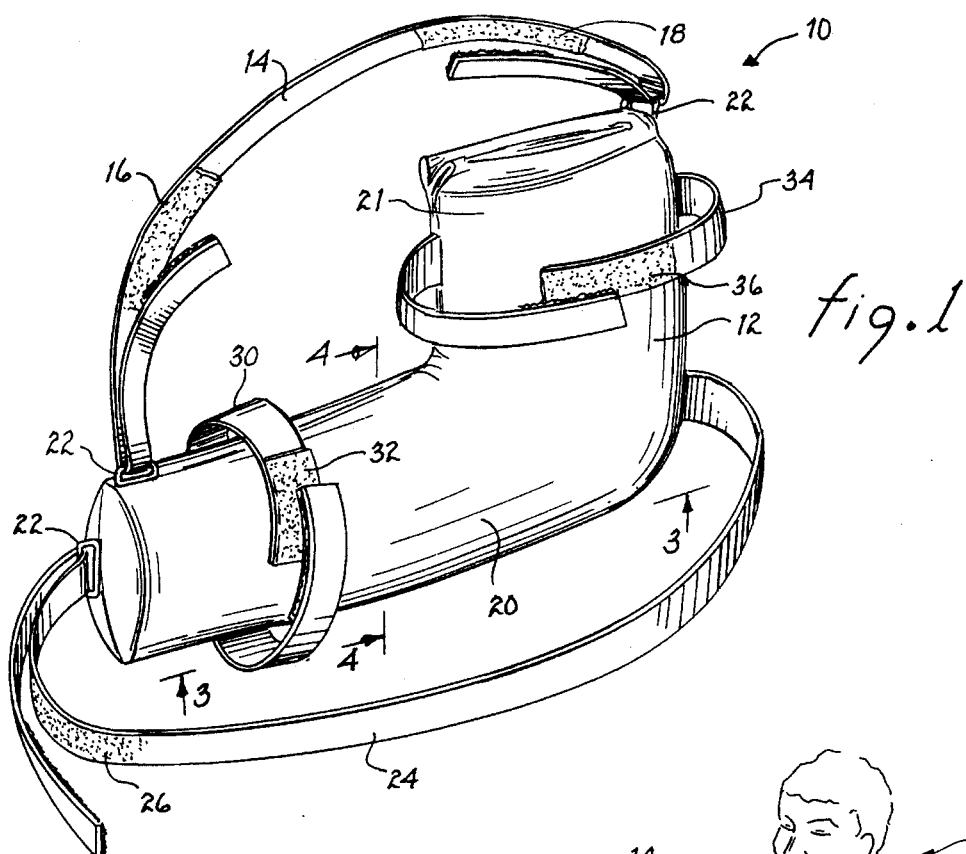
FIG. 1 is a perspective view of the preferred embodiment of the arm and shoulder support device.

Referring to FIG. 1, a portable, reversible, arm and shoulder, pillow, support device 10, or simply, support device 10, is provided. The support device 10 is comprised of a pillow support 12 and a securing portion which is further comprised of a first strap portion 14, 24 for attaching the pillow support 12 to a patient's upper torso and a second strap portion 30, 34 for attaching the pillow support 12 to the patient's arm. The pillow support 12 is comprised of a long member 20 coupled to a short member 21 forming an L-shape and D-rings 22 coupled to pillow support 12 providing attachments for various straps to the pillow support 12, as described more fully below.

The first strap portion 14, 24 is specifically comprised of a shoulder strap 14 and a waist strap 24. The shoulder strap 14 is looped at one end thereof through a D-ring 22. This end of shoulder strap 14 further carries a hook and loop assembly 16, commonly known under the tradename VELCRO, for securing shoulder strap 14 to D-ring 22. The hook and loop assembly 16 further provides a means for adjusting the length of shoulder strap 14 to the patient's preference. Similarly, the opposite end of shoulder strap 14 carries a hook and loop assembly 18 for securing it to the second D-ring 22 and for providing a second means for adjusting the length of shoulder strap 14. Both ends of shoulder strap 14 are provided with hook and loop assemblies 16 and 18 as the means for securing it to the pillow means 12 in order to provide the option of completely removing the shoulder strap 14 from the support device 10. An embodiment with the shoulder strap 14 removed is shown in FIG. 7 and described below.

Waist strap 24 is coupled at one end to a back portion of pillow support 12 near the intersection of long member 20 and short member 21. The opposite end of waist strap 24 is similar to either end of shoulder strap 14 wherein it is looped through D-ring 22 and is provided with hook and loop assembly 26 for adjustably securing the support device 10 to the patient's upper torso.

The second strap portion 30, 34 is specifically comprised of forearm strap 30 and upper arm strap 34. Forearm strap 30 is comprised of hook and loop assembly 32, whereby a hook strip portion is carried on one side of one end of the strap 30 and a mating loop strip portion is carried on one side of the opposite end of strap 30. Forearm strap 30 is wrapped around long member 20 and the patient's forearm and is secured with the hook and loop assembly 32. Additionally, forearm strap 30 is not attached to pillow support means 12. This allows the patient to secure his forearm to any location along the long member 20 of pillow support 12 depending on the patient's size and preference. Upper arm strap 34 is comprised of a first short strap portion whereby one end is coupled to an inner portion of short member 21 and a second short strap portion whereby one of its ends is coupled to an outer portion of short member 21. The uncoupled ends of the first and second short strap portions carry hook and loop assembly 36 for securing the upper arm to the pillow support 12.

It should be understood that support device 10 is reversible and may be used to support and stabilize either a patient's right arm and/or shoulder or a patient's left arm and/or shoulder.

Figure 2:
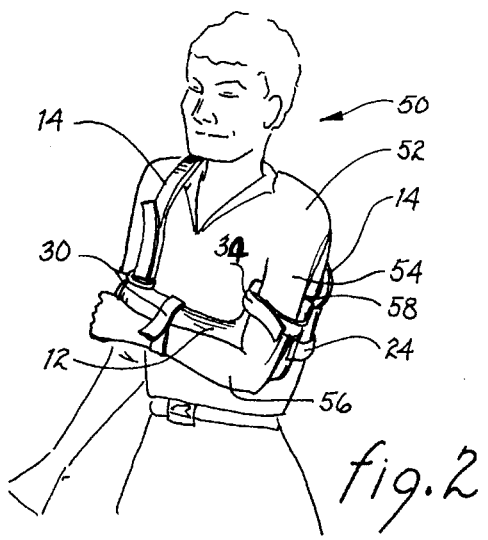
FIG. 2 is a perspective view of the support device of FIG. 1 as worn by a person in the upright position.

Referring to FIG. 2, patient 50 is wearing the support device 10 of FIG. 1 to support and stabilize his left arm 54 and left shoulder 52 while the patient 50 is in the upright position. Specifically, upper arm strap 34 is wrapped around the upper arm 58 to secure it to the short member 21. Forearm strap 30 secures the patient's forearm 56 to the desired location along long member 20. Waist strap 24 is wrapped around the waist and back of patient 50 and tightened and secured through the hook and loop assembly 26 and D-ring 22 (not shown in FIG. 2). Waist strap 24 secures and immobilizes the patient's arm 54 to the patient's upper torso. Shoulder strap 14 is placed over the right shoulder of patient 50 and crosses over to the left portion of his back. Shoulder strap 14 positions and holds forearm 56 at a desired angle relative to the upper arm 58. In this embodiment, forearm 56 is bent at approximately a 90 degree angle with respect to upper arm 58. Taken together, the securing portions 14, 24, 30 and 34 serve to hold, secure and comfortably immobilize the left arm 54 of patient 50, thereby comfortably immobilizing his left shoulder 52 as well.

Figure 3:
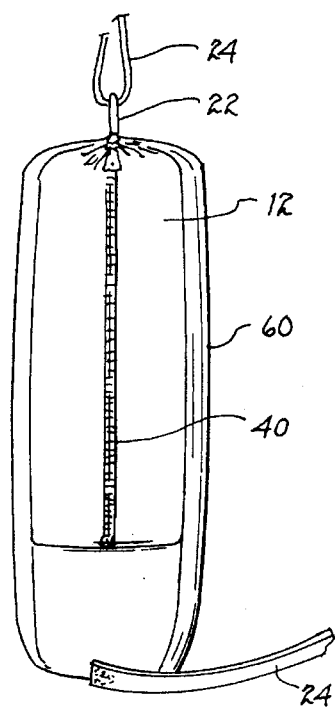
FIG. 3 is bottom view of the support device of FIG. 1 taken along the line 3—3 showing a zipper access on the outer casing.

Referring to FIG. 3, the bottom portion outer casing 60 of pillow support 12, comprising zipper 40, is disclosed. The zipper 40 allows for access to and removal of the inner material (not shown in FIG. 3) of pillow support 12 from the outer casing 60 so that the outer casing 60 may be cleaned. After cleaning and drying the outer casing 60, the inner material may be easily reinserted and zipped closed.

Referring to FIG. 4, a cross sectional view of a portion of pillow support 12, taken along the 4—4 line of FIG. 1, is provided. The outer casing 60 contains an inner material comprised of fiberfill material 64 contained in a cotton casing 62. Alternatively, the inner material may be comprised of a pre-formed foam material with or without casing 62. Utilizing pre-formed foam material as the inner material provides the benefit of eliminating the need for a casing 62 because, unlike fiberfill material, foam material holds its own shape without external support. Pillow support 12 may be manufactured in a variety of thicknesses resulting in a plurality of support devices 10, each providing a different abduction angle between the patient's arm and upper torso. Offering more than one support device 10 having different abduction angles provides the attending physician or patient the option of selecting the the support device 10 best suited to the patient's conditions and needs.

Referring to FIG. 5, an alternative embodiment of the inner material of pillow support 12 is disclosed. It is comprised of an inflatable air balloon 70 and nozzle 72 for inflating and deflating the air balloon 70. The advantage of this embodiment is that pillow support 12 may be inflated to varying degrees determined by the patient's preference or physician's prescription. As the degree of inflation increases, the inflatable air balloon 70 becomes harder or stiffer and the abduction angle formed between the arm and upper torso also increases. In essence, this embodiment allows a single support device 10 to be customized to the patient's needs.

Referring to FIG. 6, a cross sectional view of the long member of the inflatable air balloon 70 of FIG. 5 (taken along the 6—6 line) is provided. It is comprised of an outer rubber-type material 80 and is filled with a gas 82, such as air, through nozzle 72.

Referring to FIG. 7, patient 100 is shown wearing the support device 10 on the left arm in the recumbent position. In this embodiment, the shoulder strap 14 is typically removed.

Figure 8:
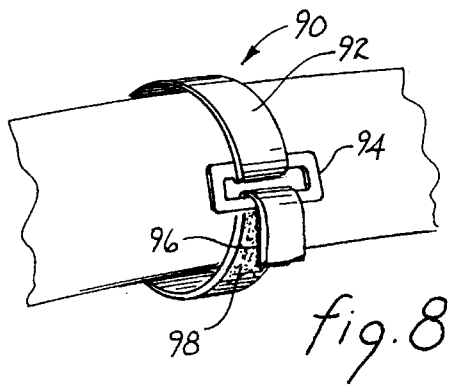
FIG. 8 is a perspective view of another embodiment of the forearm strap of the support device of FIG. 1.

Referring to FIG. 8, a perspective view of forearm strap 90 is shown. Forearm strap 90 is comprised of strap portion 92 fixedly coupled at one end thereof to buckle 94. A hook portion 96 and loop portion 98 are attached, one next to the other, to the same side of strap portion 92 starting at its second end thereof. When attaching the forearm to the pillow support 12, the patient loops the second end of strap portion 92 of forearm strap 90 through the buckle 92 and folds the end of strap 90 back over the end of buckle 92 so that hook portion 96 may meet and secure to loop portion 98 for securing forearm strap 90 to both the forearm and pillow support 12. Forearm strap 90 may be used in place of forearm strap 30 shown in FIG. 1 and described above. The advantage of forearm strap 90 is that it enables the patient to use his available, uninjured hand to easily and firmly secure forearm strap 90 to the injured arm and pillow support 12.

Referring to FIG. 9, a perspective view of waist strap 100 is provided. Waist strap 100 is similar to waist strap 24 shown in FIG. 1 with the following difference: Waist strap 100 is not fixedly coupled at one end to a back portion of pillow support 12 near the intersection of long member 20 and short member 21. Instead, a short strap portion 102 is fixedly coupled at one end thereof to the back portion of pillow support 12 near the intersection of long member 20 and short member 21. The second end of short strap portion 102 is fixedly connected to buckle 104. Waist strap 100 is looped through buckle 104 to secure itself through hook and loop assembly 106 and is therefore removable. As the opposite end of waist strap 100 is also removable, waist strap 100 can attached to pillow support 12 for use on either an injured right arm and/or shoulder or left arm and/or shoulder.

While the invention has been particularly shown and described with reference to the preferred embodiments thereof, it will be understood by those skilled in the art that the foregoing and other changes in form and details may be made therein without departing from the spirit and scope of the invention.

What is claimed is:

1. An orthopedic pillow device for supporting and immobilizing a patient's arm relative to a patient's shoulder, comprising, in combination:

portable, reversible, pillow support means for selective attachment to one of the patient's right arm and left arm and the patient's upper torso, said support means comprising L-shape pillow means, having a substantially elliptical cross-sectional shaped pillow configuration, for being configured to extend in an L-shaped configuration from just below a person's armpit to about the end of a person's hand for providing support and cushioning for both a lower and upper portion of the arm selected for support and for providing abduction of said lower and upper portions of the arm selected for support with respect to said upper torso for reducing joint stress of said shoulder; said support means having a thickness along its L-shaped configuration and an outer surface portion means for supporting an inner portion of said selected arm extending substantially in one plane downward and in an L-shaped configuration from the armpit of said selected arm to said upper and said lower portions of said selected arm and an inner surface portion means for extending inwardly from the armpit of said selected arm and in said L-shaped configuration parallel to and adjacent to a front portion of a person's torso; and securing means coupled to said support means for securing said support means to both said patient's arm and said upper torso.

2. The device of claim 1 wherein said support means comprises an inner material having a long member coupled at one end thereof to one end of a short member forming an L-shape, and an outer casing conforming to said L-shape of said inner material for containing said inner material.

3. The device of claim 2 wherein said inner material is a material selected from a group consisting of a pre-formed foam material and a fiberfill material stuffed in a casing.

4. The device of claim 2 wherein said inner material comprises an inflatable air bladder.

5. The device of claim 2 wherein said outer casing comprises zipper means for providing access to said inner material for removing said inner material from said outer casing.

6. The device of claim 2 wherein said securing means comprises first strap means for securing said support means to said patient's upper torso and second strap means for securing said support means to said patient's arm.

7. The device of claim 6 wherein said first strap means comprises a waist strap coupled to said long member of said support means for securing to a portion of said patient's waist and a shoulder strap coupled at one end thereof to an end of said long member not coupled to said short member and coupled at the other end thereof to an end of said short member not coupled to said long member for securing said support means to said patient's shoulder.

8. The device of claim 7 wherein said shoulder strap is removable.

9. The device of claim 6 wherein said second strap means comprises an upper arm strap coupled to said short member for securing an upper portion of said arm to said support means and a forearm strap coupled to said long member for securing a portion of said patient's forearm to said support means.

10. The device of claim 9 wherein said forearm strap is removably connected to said long member of said support means for placement at substantially any location along said long member.

11. A method for providing an orthopedic pillow device for supporting an immobilizing a patient's arm relative to a patient's shoulder comprising the steps of:

providing a portable, reversible, pillow support means for selective attachment to one of the patient's right arm and left arm and the patient's upper torso, said support means comprising L-shape pillow means, having a substantially elliptical cross-sectional shaped pillow configuration, for being configured to extend in an L-shaped configuration from just below a person's armpit to about the end of a person's hand for providing support and cushioning for both a lower and upper portion of the arm selected for support and for providing abduction of said lower and upper portions of the arm selected for support with respect to said suppport means having a thickness along its L-shaped configuration and an outer surface portion means for supporting an inner portion of said selected arm extending substantially in one plane downward and in an L-shaped configuration from the armpit of said selected arm to said upper and said lower portions of said selected arm and an inner surface portion means for extending inwardly from the armpit of said selected arm and in said L-shaped configuration parallel to and adjacent to a front portion of a person's torso; and coupling securing means to said support means for securing said support means to both said patient's arm and said upper torso.

12. The method of claim 11 wherein said support means comprises an inner material having a long member coupled at one end thereof to one end of a short member forming an L-shape, and an outer casing conforming to said L-shape of said inner material for containing said inner material.

13. The method of claim 12 wherein said inner material is a material selected from a group consisting of a pre-formed foam material and fiberfill material stuffed in a casing.

14. The method of claim 12 wherein said inner material comprises an inflatable air bladder.

15. The method of claim 12 wherein said outer casing comprises zipper means for providing access to said inner material for removing said inner material from said outer casing.

16. The method of claim 12 wherein said securing means comprises first strap means for securing said support means to said patient's upper torso and second strap means for securing said support means to said patient's arm.

17. The method of claim 16 wherein said first strap means comprises a waist strap coupled to said long member of said support means for securing to a portion of said patient's waist and a shoulder strap coupled at one end thereof to an unconnected end of said long member and coupled at the other end thereof to an unconnected end of said short member for securing said support means to said patient's shoulder.

18. The method of claim 17 wherein said shoulder strap is removable.

19. The method of claim 16 wherein said second strap means comprises an upper arm strap coupled to said short member for securing an upper portion of said arm to said support means and a forearm strap coupled to said long member for securing a portion of said patient's forearm to said support means.

20. The method of claim 19 wherein said forearm strap is removably connected to said long member of said support means for placement at any location along said long member.

* * * * *

UNITED STATES PATENT AND TRADEMARK OFFICE
CERTIFICATE OF CORRECTION

PATENT NO. : 5,464,383

DATED : November 7, 1995

INVENTOR(S) : Padden et al.

It is certified that error appears in the above-identified patent and that said Letters Patent is hereby corrected as shown below:

Column 7:

Claim 11, line 2, change "an" to -- and --.

Claim 11, line 15, after "said" insert -- upper torso for reducing joint stress of said shoulder, said --.

Signed and Sealed this

Twenty-sixth Day of March, 1996

Attest:

BRUCE LEHMAN

Attesting Officer

Commissioner of Patents and Trademarks